(12) United States Patent
McMahon et al.

(10) Patent No.: US 11,235,075 B2
(45) Date of Patent: Feb. 1, 2022

(54) PEPTIDE HYDROGELS GENERATING CHEMICAL EXCHANGE SATURATION TRANSFER MRI CONTRAST AND USES THEREOF

(71) Applicants: THE JOHNS HOPKINS UNIVERSITY, Baltimore, MD (US); KENNEDY KRIEGER INSTITUTE, INC., Baltimore, MD (US); NATIONAL INSTITUTES OF HEALTH, Bethesda, MD (US)

(72) Inventors: Michael T. McMahon, Columbia, MD (US); Kannie Wai-Yan Chan, Baltimore, MD (US); Michael Christopher Giano, Frederick, MD (US); Nikita Oskolkov, Reisterstown, MD (US); Joel Patrick Schneider, Frederick, MD (US); Xiaolei Song, Lutherville, MD (US)

(73) Assignees: THE JOHNS HOPKINS UNIVERSITY, Baltimore, MD (US); KENNEDY KRIEGER INSTITUTE, INC., Baltimore, MD (US); NATIONAL INSTITUTES OF HEALTH, Bethesda, MD (US)

( * ) Notice: Subject to any disclaimer, the term of this patent is extended or adjusted under 35 U.S.C. 154(b) by 89 days.

(21) Appl. No.: 14/787,039

(22) PCT Filed: Apr. 28, 2014

(86) PCT No.: PCT/US2014/035651
§ 371 (c)(1),
(2) Date: Oct. 26, 2015

(87) PCT Pub. No.: WO2014/176586
PCT Pub. Date: Oct. 30, 2014

(65) Prior Publication Data
US 2016/0106871 A1    Apr. 21, 2016

Related U.S. Application Data

(60) Provisional application No. 61/816,322, filed on Apr. 26, 2013.

(51) Int. Cl.
*A61B 5/055* (2006.01)
*A61K 49/18* (2006.01)
*A61K 49/14* (2006.01)

(52) U.S. Cl.
CPC .......... *A61K 49/1803* (2013.01); *A61K 49/14* (2013.01)

(58) Field of Classification Search
None
See application file for complete search history.

(56) References Cited

U.S. PATENT DOCUMENTS

| | | | |
|---|---|---|---|
| 7,884,185 B2 * | 2/2011 | Schneider | A61K 41/0042 530/326 |
| 2009/0175785 A1 * | 7/2009 | Gazit | A61L 27/227 424/1.29 |
| 2013/0079421 A1 * | 3/2013 | Aviv | A61L 27/20 514/773 |

OTHER PUBLICATIONS

Chan, K., et al., "MRI-detectable pH nanosensors incorporated into hydrogels for in vivo sensing of transplanted-cell viability", Nature Materials, Mar. 2013, vol. 12, pp. 268-275.
Liang, Y., et al., "CEST imaging reveals dynamic changes of implanted hydrogel scaffold in vivo", Proc. Intl. Soc. Mag. Reson. Med. (2011) vol. 19, pp. 316.
Liu, G., et al., "In vivo multicolor molecular MR imaging using diamagnetic chemical exchange saturation transfer liposomes", Magnetic Resonance in Medicine (2012) vol. 67, pp. 1106-1113.
McMahon, M., et al., "New multicolor polypeptide diamagnetic chemical exchange saturation transfer (DIACEST) contrast agents for MRI", Magnetic Resonance in Medicine (2008) vol. 60, pp. 803-812.

* cited by examiner

*Primary Examiner* — Michael G. Hartley
*Assistant Examiner* — Melissa J Perreira
(74) *Attorney, Agent, or Firm* — Casimir Jones, S.C.; Kelly A. Barton

(57) ABSTRACT

The present invention provides novel hydrogels through peptides, which are designed to self-assemble and produce magnetic resonance (MR) contrast through chemical exchange saturation transfer (CEST). The location and integrity of these gels could consequently be tracked using MR imaging. The self-assembly of the peptides into hydrogels can be brought about by a change in pH, ionic strength, temperature, and concentration of ions.

12 Claims, No Drawings

PEPTIDE HYDROGELS GENERATING CHEMICAL EXCHANGE SATURATION TRANSFER MRI CONTRAST AND USES THEREOF

CROSS-REFERENCE TO RELATED APPLICATIONS

This application is a 35 U.S.C. § 371 U.S. national entry of International Application PCT/US2014/035651, having an international filing date of Apr. 28, 2014, which claims the benefit of U.S. Provisional Application No. 61/816,322, filed Apr. 26, 2013, the content of each of the aforementioned applications is herein incorporated by reference in their entirety.

GOVERNMENT SUPPORT

This invention was made with government support under R01 EB015031 and 1R01EB012590 both awarded by the National Institutes of Health. The government has certain rights in the invention.

FIELD OF THE INVENTION

The present invention relates generally to medical imaging. More particularly the present invention relates to non-metallic CEST contrast agents for use in magnetic resonance imaging.

BACKGROUND OF THE INVENTION

Currently, two major classes of MR contrast agents are in routine use: paramagnetic agents (e.g. chelates of Gd or Mn, or Mn particles), producing large positive signal enhancement from decreasing $T_1$, and superparamagnetic agents, such as iron oxide particles, which produce large negative $T_2$ contrast. These contrast agents contain paramagnetic metals that need to be administered in relatively high doses (compared to PET/SPECT and optical methods). The safety of these metals has recently been questioned. MR contrast agents that contain Gd may be toxic to the kidneys, raising concerns since these agents typically are administered in relatively high doses or when they stay around longer, raising the risk of metal release. MR agents based on paramagnetic metals also have the significant limitation that they provide only one type of contrast (signal intensity change). If it were instead possible to develop bioorganic biodegradable compounds tailored for multi-color MRI detection, it may be possible to gather information regarding delivery efficiency and persistence in a safe manner that allows simultaneous tracking of more than one drug/nanoparticle.

Another type of MRI contrast has been developed called Chemical Exchange Saturation Transfer (CEST). CEST agents have exchangeable protons with different characteristic MR frequencies (multiple "colors") that can be used to selectively highlight different tissues and agents (e.g., tumor and nanoparticles) simultaneously.

Recently, more classes of MR agents have become available, such as based on magnetic isotope labeling (e.g. F "hot spot" imaging using particles loaded with perfluorocarbons), and so-called chemical exchange saturation transfer (CEST) contrast agents. CEST agents are especially powerful in that they can be selectively labeled using frequency-specific radio-frequency (rf) saturation of exchangeable protons on the agents. Chemical exchange causes these protons to transfer this saturation to water protons. Because the water proton pool is very large, unlabeled water protons move back to the agent and the process repeats itself, leading to large sensitivity enhancements, ultimately allowing MRI detection. Paramagnetic agents with appropriately shifted exchangeable groups, termed "PARACEST" agents can also be used in MR. CEST can detect micromolar concentrations of polypeptide gene carriers and close to nanomolar concentrations of polynucleotides. These non-metallic diamagnetic compounds are called DIACEST agents.

Since the first report of chemical exchange saturation transfer (CEST) contrast in 2000, this imaging technology has attracted many new research studies, resulting in a number of preclinical and now also clinical applications. Endogenous CEST contrast has been applied to characterizing acute ischemia and brain tumors, visualizing the concentration of tissue amide protons and their chemical exchange rate. CEST contrast has been found to relate to tumor grade, and allows separation of recurrent tumor from the effects of treatment. This contrast is also used in musculoskeletal imaging for monitoring glycosaminoglycan concentrations in cartilage. In addition, CEST reporter genes are being developed allowing detection of cells expressing this gene.

An important advantage of CEST is the capability to design agents with protons at different frequencies, allowing simultaneous detection of probes with different functions. CEST probes have been designed to label virus particles, allow imaging of the kidneys, and allow the detection of peptides, drug delivery particles, changes in temperature, pH, and metabolite concentrations. Ultimately, for both endogenous and exogenous CEST contrast agent studies, improved detection technologies will be important to speed up the transition to widespread preclinical and clinical use.

It would therefore be advantageous to provide a non-metallic contrast agent for use with CEST magnetic resonance imaging.

SUMMARY

According to a first aspect of the present invention, an agent for use in conjunction with magnetic resonance (MR) imaging includes a biocompatible chemical exchange saturation transfer (CEST) agent. The biocompatible CEST agent takes the form of a peptide-based hydrogel. The biocompatible CEST agent is also configured to create contrast in an MR image detectable using a saturation transfer CEST method of MR imaging.

In accordance with an aspect of the present invention, the peptide-based hydrogel further includes at least one of lysine, argenine, ornithine, serine, threonine, histidine, tryptophan, and unnatural amino acids containing heterocyclic protons. The peptide-based hydrogel produces a chemical shift of between approximately 1-15 ppm downfield from water. The peptide-based hydrogel produces suitable exchange rates for generating CEST contrast in an MR machine. The peptide-based hydrogel further comprises exchangeable protons. The peptide-based hydrogel includes two β-strands composed of alternating hydrophobic and hydrophilic residues flanking a tetrapeptide turn sequence. The hydrophobic residues comprise valine, and the hydrophilic residue is one selected from a group consisting of histidine, serine or aspartate. The tetrapeptide turn sequence can take the form of 'Val-pro-Pro-Thr'. The contents of the peptide based hydrogel are selected based on diffusion time, patient pH, biodegradability.

In accordance with another aspect of the present invention, a method for magnetic resonance imaging of a subject includes providing a biocompatible CEST contrast agent formed from a peptide-based hydrogel. The method includes delivering the biocompatible CEST contrast agent to the subject. Additionally, the method includes using a CEST method of MR imaging to obtain an MR image of the subject.

In accordance with still another aspect of the present invention, the method includes providing the peptide-based hydrogel with at least one of lysine, argenine, ornithine, serine, threonine, histidine, tryptophan, and unnatural amino acids containing heterocyclic protons. The method includes providing the peptide-based hydrogel such that it produces a chemical shift of between approximately 1-15 ppm downfield from water. The method includes providing the peptide-based hydrogel such that it produces suitable exchange rates for generating CEST contrast in an MR machine. Additionally, the method includes providing the peptide-based hydrogel comprising exchangeable protons. The method also includes providing the peptide-based hydrogel comprising two β-strands composed of alternating hydrophobic and hydrophilic residues flanking a tetrapeptide turn sequence. The method also includes providing the peptide-based hydrogel wherein the hydrophobic residues comprise valine, and providing the peptide-based hydrogel wherein the hydrophilic residue is one selected from a group consisting of histidine, serine or aspartate. The method includes providing the peptide-based hydrogel wherein the tetrapeptide turn sequence comprises 'Val-pro-Pro-Thr'. The peptide based hydrogels can be chosen based on diffusion time, patient pH, biodegradability.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention provides novel hydrogels through peptides, which are designed to self-assemble and produce magnetic resonance (MR) contrast through chemical exchange saturation transfer (CEST). The location and integrity of these gels could consequently be tracked using MR imaging. The self-assembly of the peptides into hydrogels can be brought about by a change in pH, ionic strength, temperature, and concentration of ions.

Metal-based theranostic systems usually have some limitations for in vivo such as toxicity or difficulties in distinguishing the metal-based contrast from other sources in the images. Non-metallic CEST agents can be substituted for gadolinium or other lanthanides as a source of contrast, which is potentially important as exposure to gadolinium in gadodiamide has been associated with a serious adverse reaction called nephrogenic systemic fibrosis (NSF) in patients. Peptide-based hydrogels are therefore ideal for MRI monitoring based around lysine, arginine, serine, threonine, histidine, tryptophan, and unnatural amino acids containing heterocyclic protons. The chemical shift of these exchangeable protons can be between 1-15 ppm downfield from water with suitable exchange rates for generating CEST contrast.

A method of obtaining MR images of a subject includes providing a biocompatible CEST contrast agent. The CEST contrast agent can be formed from a peptide-based hydrogel. The monitoring can be done around lysine, arginine, serine, threonine, histidine, tryptophan, and unnatural amino acids containing heterocyclic protons. The biocompatible CEST contrast agent is delivered to the subject, and a CEST method of MR imaging is used to obtain an MR image of the subject.

The present invention incorporates peptides with exchangeable protons into peptides within a well-known self-assembling peptide hydrogel system. Specifically, two β-strands composed of alternating hydrophobic (valine) and hydrophilic (histidine, serine or aspartate) residues flank a tetrapeptide turn sequence 'Val-pro-Pro-Thr' that has the ability to self-assemble into hydrogels. These exchangeable protons can be those found in lysine, arginine, ornithine, threonine or serine, as these have suitable to produce contrast or heterocyclic protons which are within a hydrogen bonding network such as found in the catalytic triad of bovine chymotrypsin-A (histidine, serine and aspartate). In addition, our method involves use of unnatural amino acids containing heterocyclic nitrogen protons to generate this contrast. Based on these elements, it should be feasible to create short peptides with strong hydrogen bonding to form hydrogels, which may respond to environmental changes such as pH and ion concentration. The chemical shift difference between exchangeable protons on the designed peptides and bulk water is in the range of 1-20 ppm. These designed peptides can produce MRI contrast and be used for a variety of applications because of their unique properties, swelling, mechanical properties, biodegradation, and diffusion.

An embodiment in accordance with the present invention provides a method for obtaining a magnetic resonance image (MRI) or spectrum. The method includes a step of performing a chemical exchange saturation transfer (CEST) magnetic labeling experiment of a subject using one of the described CEST agents and an MRI machine. During the period of time for performing the CEST magnetic labeling experiment an aspect of the acquisition, such as a saturation pulse or series pulse sequence applied by the MRI machine can be varied. Data is generated from the CEST magnetic labeling experiment and is transmitted to a data processing unit. The data is processed to generate a visual representation of the data.

As noted above the peptides incorporated into the contrast agent hydrogel can have special properties. These special properties can then be used based on the needs of the patient and the image desired. The CEST agent can be chosen based on diffusion time, patient pH, biodegradability, etc.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. An agent for use in conjunction with magnetic resonance (MR) imaging comprising:
    a biocompatible chemical exchange saturation transfer (CEST) agent;
    wherein said biocompatible CEST agent takes the form of a peptide-based hydrogel comprising two β-strands comprising alternating hydrophobic and hydrophilic residues flanking a tetrapeptide turn sequence, wherein the hydrophobic residues comprise valine, each hydrophilic residue is selected from a group consisting of histidine, serine and aspartate, and the tetrapeptide turn sequence comprises 'Val-pro-Pro-Thr'; and wherein said peptide-based hydrogel is inherently a contrast agent; and
    wherein said biocompatible CEST agent is configured to create contrast in an MR image detectable using a saturation transfer CEST method of MR imaging.

2. The agent of claim 1 wherein the peptide-based hydrogel further comprises at least one of lysine, arginine, ornithine, serine, threonine, histidine, tryptophan, and unnatural amino acids containing heterocyclic protons.

3. The agent of claim 1 wherein the peptide-based hydrogel produces a chemical shift of between approximately 1-15 ppm downfield from water.

4. The agent of claim 1 wherein the peptide-based hydrogel produces suitable exchange rates for generating CEST contrast in an MR machine.

5. The agent of claim 1 wherein the peptide-based hydrogel further comprises exchangeable protons.

6. The agent of claim 1 wherein the contents of the peptide based hydrogel are selected based on diffusion time, patient pH, biodegradability.

7. A method for magnetic resonance (MR) imaging of a subject comprising:
    providing an agent as in claim 1
    delivering the agent to the subject; and
    using a chemical exchange saturation transfer agent (CEST) method of MR imaging to obtain an MR image of the subject.

8. The method of claim 7 wherein the peptide-based hydrogel comprises at least one of lysine, arginine, ornithine, serine, threonine, histidine, tryptophan, and unnatural amino acids containing heterocyclic protons.

9. The method of claim 7 wherein the peptide-based hydrogel produces a chemical shift of between approximately 1-15 ppm downfield from water.

10. The method of claim 7 wherein the peptide-based hydrogel produces suitable exchange rates for generating CEST contrast in an MR machine.

11. The method of claim 7 wherein the peptide-based hydrogel comprises exchangeable protons.

12. The method of claim 7 further comprising selecting the peptide based hydrogel based on diffusion time, patient pH, biodegradability.

* * * * *